US005716819A

United States Patent [19]
Chatterjee

[11] Patent Number: 5,716,819
[45] Date of Patent: Feb. 10, 1998

[54] CLONING AND EXPRESSION OF T5 DNA POLYMERASE REDUCED IN 3'-TO-5' EXONUCLEASE ACTIVITY

[75] Inventor: Deb K. Chatterjee, Gaithersburg, Md.

[73] Assignee: Life Technologies, Inc., Rockville, Md.

[21] Appl. No.: 688,176

[22] Filed: Jul. 29, 1996

Related U.S. Application Data

[60] Division of Ser. No. 494,531, Mar. 16, 1990, Pat. No. 5,541,099, which is a continuation-in-part of Ser. No. 391,930, Aug. 10, 1989, Pat. No. 5,047,342.

[51] Int. Cl.$^6$ .............................. C12N 15/22; C12N 1/21; C12N 9/12; C12N 9/16
[52] U.S. Cl. ............... 435/194; 435/196; 435/252.3; 435/254.11; 435/320.1; 435/325; 536/23.2; 536/24.1
[58] Field of Search ................................ 435/194, 196, 435/252.3, 254.11, 320.1, 325; 536/23.2, 24.1

[56] References Cited

U.S. PATENT DOCUMENTS

| | | | |
|---|---|---|---|
| 4,394,443 | 7/1983 | Weissman et al. | 435/6 |
| 4,689,406 | 8/1987 | Banks et al. | 536/24.1 |
| 4,766,066 | 8/1988 | Kuhstoss et al. | 435/69.3 |
| 4,795,699 | 1/1989 | Tabor et al. | 435/5 |
| 4,889,818 | 12/1989 | Gelfand et al. | 435/194 |
| 5,047,342 | 9/1991 | Chatterjee | 435/194 |
| 5,102,802 | 4/1992 | McAllister | 435/252.33 |
| 5,108,892 | 4/1992 | Burke et al. | 435/6 |
| 5,270,179 | 12/1993 | Chatterjee | 435/69.1 |
| 5,541,099 | 7/1996 | Chatterjee | 435/194 |

FOREIGN PATENT DOCUMENTS

| | | |
|---|---|---|
| 0 265 293 | 4/1988 | European Pat. Off. |
| WO 89/06691 | 7/1989 | WIPO |

OTHER PUBLICATIONS

Bernad, A. et al., "A Conserved 3'→5' Exonuclease Active Site in Prokaryotic and Eukaryotic DNA Polymerases," *Cell* 59:219–228 (Oct. 1989).

Boswell, D. R., and A. M. Lesk, "Sequence comparison and alignment: the measurement and interpretation of sequence similarity," in: *Computational Molecular Biology: Sources and Methods for Sequence Analysis*, A. M. Lesk, Ed., Oxford University Press, Oxford, pp.161–163 (Feb. 1989).

Chatterjee, D. K. et al., "Cloning and overexpression of the gene encoding bacteriophage T5 DNA polymerase," *Gene* 97:13–19 (1991).

Creighton, T. E., in: *Proteins: Structures and Molecular Properties, Second Edition*, W. H. Freeman and Co., New York, N. Y., pp. 93–95 (1993).

Das, S. K. et al., "Effect of Mg.CTP$^{2-}$ and Mg.GTP$^{2-}$ on the 3'→5' Exonuclease Activity of T5-Induced DNA Polymerase," *J. Carbohydrates, Nucleosides, Nucleotides* 5(5):457–467 (1978).

Das, S. K. et al., "Effect of magnesium CTP(2–) and magnesium GTP(2–) on the 3'→5' exonuclease activity of T5-induced DNA polymerase," *Chem. Abstr.* 91:194, Abstract No. 1841r (1979).

Das, S. K. and R. K. Fujimura, "Mechanism of T5-induced DNA Polymerase: Replication of Short Primer Templates," *J. Biol. Chem.* 252(23):8700–8707 (1977).

Das, S.K. and R. K. Fujimura, "Mechanism of Primer–Template–dependent Conversion of dNTP→dNMP by T5 DNA Polymerase," *J. Biol. Chem.* 255(15):7149–7154 (1980).

Das, S. K. and R. K. Fujimura, "Processiveness of DNA Polymerases: A Comparative Study Using a Simple Procedure," *J. Biol. Chem.* 254(4):1227–1232 (1979).

Donlin, M. J. et al., "Kinetic Partitioning between the Exonuclease and Polymerase Sites in DNA Error Correction," *Biochem.* 30:538–546 (1991).

Fujimura, R. K. and B. C. Roop, "Characterization of DNA Polymerase Induced by Bacteriophage T5 with DNA Containing Single Strand Breaks," *J. Biol. Chem.* 251(7):2168–2175 (1976).

Fujimura, R. K. et al., "Physical Locus of the DNA Polymerase Gene and Genetic Maps of Bacteriophage T5 Mutants," *J. Virol.* 53(2):495–500 (1985).

Johnson, K. A. et al., "Elementary Steps of DNA Polymerization," *DNA–Protein Interactions: Eighth Summer Symposium in Molecular Biology*:44, 60–62 (Jul. 1989).

Joyce, C. M. and T. A. Steitz, "DNA polymerase I: from crystal structure to function via genetics", *Trends Biochem. Sci.* 12:288–292 (1987).

Kozak, M., "Comparison of Initiation of Protein Synthesis in Procaryotes, Eucaryotes, and Organelles," *Microbiol. Rev.* 47(1):1–45 (1983).

Leavitt, M. C. and J. Ito, "T5 DNA polymerase: Structural–functional relationships to other DNA polymerases," *Proc. Natl. Acad. Sci. USA* 86:4465–4469 (Jun. 1989).

Lewin, R., "When Does Homology Mean Something Else?" *Science* 237:1570 (1987).

Lin, T.-C. et al., "Cloning and expression of T4 DNA polymerase," *Proc. Natl. Acad. Sci. USA* 84:7000–7004 (1987).

Minkley, E. G. et al., "*Escherichia coli* DNA Polymerase I: Construction of a polA Plasmid for Amplification and an Improved Purification Scheme," *J. Biol. Chem.* 259(16):10386–10392 (1984).

(List continued on next page.)

*Primary Examiner*—Stephen Walsh
*Assistant Examiner*—Brian Lathrop
*Attorney, Agent, or Firm*—Sterne, Kessler, Goldstein & Fox P.L.L.C.

[57] ABSTRACT

The present invention discloses a recombinant DNA molecule having a structural gene encoding a processive, thioredoxin-independent DNA polymerase that is substantially reduced in processive 3'-to-5' DNA exonuclease activity, a promoter, and an origin of replication. A method for producing this enzyme is also disclosed, as is the protein produced by this process. This invention is exemplified by expression of exonuclease$^-$ T5 DNA polymerase in *E. coli*.

21 Claims, 7 Drawing Sheets

OTHER PUBLICATIONS

Patel, S. S. et al., "Pre-Steady-State Kinetic Analysis of Processive DNA Replication Including Complete Characterization of an Exonuclease-Deficient Mutant," *Biochem.* 30:511-525 (1991).

Reeck, G. R. et al., "'Homology' in Proteins and Nucleic Acids: A Terminology Muddle and a Way out of It," *Cell* 50:667 (1987).

Reha-Krantz, L. J. et al., "DNA polymerization in the absence of exonucleolytic proofreading: In vivo and in vitro studies," *Proc. Natl. Acad. Sci. USA* 88:2417-2421 (1991).

Remaut, E. et al., "Plasmid vectors for high-efficiency expression controlled by the $P_L$ promoter of coliphage lambda," *Gene* 15:81-93 (1981).

Rhoades, M., "New Physical Map of Bacteriophage T5 DNA," *J. Virol.* 43(2):566-573 (1982).

Shibui, T. et al., "A New Hybrid Promoter and Its Expression Vector in *Escherichia coli*," *Agric. Biol. Chem* 52(4):983-988 (Apr. 1988).

Spicer, E. K. et al., "Primary Structure of T4 DNA Polymerase: Evolutionary Relatedness to Eucaryotic and Other Procaryotic DNA Polymerases," *J. Biol. Chem.* 263(16):7478-7486 (Jun. 1988).

Stark, M. J. R., "Multicopy expression vectors carrying the lac repressor gene for regulated high-level expression of genes in *Escherichia coli*," *Gene* 51:255-267 (1987).

Stueber, D. et al., "A novel in vitro transcription-translation system: accurate and efficient synthesis of single proteins from cloned DNA sequences," *EMBO J.* 3(13):3143-3148 (1984).

Tabor, S., and C. C. Richardson, "Selective Inactivation of the Exonuclease Activity of Bacteriophage T7 DNA Polymerase by in Vitro Mutagenesis," *J. Biol. Chem.* 264(11):6447-6458 (Apr. 1989).

Watson, J. D. et al., "Recombination at the Molecular Level," in: *Molecular Biology of the Gene Fourth Edition*, The Benjamin/Cummings Publishing Company, Inc., Menlo Park, CA, pp. 313-338 (1987).

Wong, I. et al., "An Induced-Fit Kinetic Mechanism for DNA Replication Fidelity: Direct Measurement by Single-Turnover Kinetics," *Biochem.* 30:526-537 (1991).

Leavitt & Ito

METTyrSerIleCysValThrArgSerCysProValCysSerLysLysHisIleThr...
...ATGTATTCCATATGTGTAACGAGAAGTTGTCCGGTCGTTGCTCAAAAAGCATATTACT...
(5')  +1 ----+----+----+----+----+----+ 60 (3')
   ...ATGTATTCCATATGTGTAACGAGAAGTTGTCCGGTCGTTGCTC-AAAAAGCATATTACT...
      METCysAsnGluLysLeuSerGlyArgLeuLeu-LysLysHisIleThr...
      corrected sequence

FIG.1

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GGTTATCGGG  CCCGTCGCAT  TCGCCTCCGC  AACCTCAGCA  C                    41
```

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: circular ( i i ) MOLECULE TYPE: cDNA ( i x ) FEATURE:
        ( A ) NAME/KEY: CDS
        ( B ) LOCATION: 1..60

( x i ) SEQUENCE DESCRIPTION: SEQ ID NO:2:

```
ATG  TAT  TCC  ATA  TGT  GTA  ACG  AGA  AGT  TGT  CCG  GTC  GTT  TGC  TCA  AAA       48
Met  Tyr  Ser  Ile  Cys  Val  Thr  Arg  Ser  Cys  Pro  Val  Val  Cys  Ser  Lys
 1             5                        10                       15

AAG  CAT  ATT  ACT                                                                    60
Lys  His  Ile  Thr
```

(2) INFORMATION FOR SEQ ID NO:3:

(i) SEQUENCE CHARACTERISTICS:
       (A) LENGTH: 20 amino acids
       (B) TYPE: amino acid
       (D) TOPOLOGY: linear (ii) MOLECULE TYPE: protein (xi) SEQUENCE DESCRIPTION: SEQ ID NO:3:

```
Met Tyr Ser Ile Cys Val Thr Arg Ser Cys Pro Val Val Cys Ser Lys
 1           5                   10                  15

Lys His Ile Thr
            20
```

(2) INFORMATION FOR SEQ ID NO:4:

(i) SEQUENCE CHARACTERISTICS:
       (A) LENGTH: 59 base pairs
       (B) TYPE: nucleic acid
       (C) STRANDEDNESS: double
       (D) TOPOLOGY: circular (ii) MOLECULE TYPE: cDNA (ix) FEATURE:
       (A) NAME/KEY: CDS
       (B) LOCATION: 12..59

(xi) SEQUENCE DESCRIPTION: SEQ ID NO:4:

```
ATGTATTCCA T ATG TGT AAC GAG AAG TTG TCC GGT CGT TTG CTC AAA AAG      50
             Met Cys Asn Glu Lys Leu Ser Gly Arg Leu Leu Lys Lys
                                 25                  30

CAT ATT ACT                                                            59
His Ile Thr
    35
```

(2) INFORMATION FOR SEQ ID NO:5:

(i) SEQUENCE CHARACTERISTICS:
       (A) LENGTH: 16 amino acids
       (B) TYPE: amino acid
       (D) TOPOLOGY: linear (ii) MOLECULE TYPE: protein (xi) SEQUENCE DESCRIPTION: SEQ ID NO:5:

```
Met Cys Asn Glu Lys Leu Ser Gly Arg Leu Leu Lys Lys His Ile Thr
 1           5                   10                  15
```

CLONING AND EXPRESSION OF T5 DNA POLYMERASE REDUCED IN 3'-TO-5' EXONUCLEASE ACTIVITY

RELATED APPLICATIONS

This application is a division of application Ser. No. 07/494,531, filed Mar. 16, 1990, now U.S. Pat. No. 5,541, 099, which is a continuation-in-part of application Ser. No. 07/391,930, filed Aug. 10, 1989, now U.S. Pat. No. 5,047, 342.

FIELD OF THE INVENTION

This invention relates to molecular cloning and expression of the DNA polymerase of the E. coli bacteriophage T5 and to production of mutants of T5 DNA polymerase substantially reduced in 3'-to-5' exonuclease activity.

BACKGROUND OF THE INVENTION

DNA polymerases synthesize the formation of DNA molecules from deoxynucleoside triphosphates using a complementary template DNA strand and a primer. DNA polymerases synthesize DNA in the 5'-to-3' direction by successively adding nucleotides to the free 3'-hydroxyl group of the growing strand. The template strand determines the order of addition of nucleotides via Watson-Crick base pairing. In cells, DNA polymerases are involved in repair synthesis and DNA replication.

Bacteriophage T5 induces the synthesis of its own DNA polymerase upon infection of its host, Escherichia coli. The T5 DNA polymerase (T5-DNAP) was purified to homogeneity by Fujimura R K & Roop B C, J. Biol. Chem. 25:2168–2175 (1976). T5-DNAP is a single polypeptide of molecular weight of about 96 kilodaltons. This polymerase is highly processive and, unlike T7 DNA polymerase, does not require thioredoxin for its processivity (Das S K & Fujimura R K, J. Biol. Chem. 252:8700–8707 (1977); Das S K & Fujimura R K, J. Biol. Chem. 254:1227–1237 (1979)).

Fujimura R K et al., J. Virol. 53:495–500 (1985) disclosed the approximate location of the T5-DNAP gene on the physical restriction enzyme map generated by Rhoades (J. Virol. 43:566–573 (1982)). DNA sequencing of the fragments of this corresponding region was disclosed by Leavitt M C & Ito J, Proc. Natl. Acad. Sci. USA 86:4465–4469 (1989). However, the authors did not reassemble the sequenced fragments to obtain expression of the polymerase.

Oligonucleotide-directed, site-specific mutation of a T7 DNA polymerase gene was disclosed by Tabor S & Richardson C C, J. Biol. Chem. 264:6447–6458 (1989). It is believed that there are no publications before the invention of the subject matter disclosed herein describing mutation of 3'-to-5' exonuclease activity of T5-DNAP.

The existence of a conserved 3'-to-5' exonuclease active site present in a number of DNA polymerases was predicted by Bernd A et al., Cell 59:219–228 (1989).

In molecular biology, DNA polymerases have several uses. In cloning and gene expression experiments, DNA polymerases are used to synthesize the second strand of a single-stranded circular DNA annealed to an oligonucleotide primer containing a mutated nucleotide sequence. DNA polymerases have also been used for DNA sequencing. Tabor & Richardson, U.S. Pat. No. 4,795,699, disclose that processive, host thioredoxin-requiring, T7-type DNA polymerases, especially those lacking substantial exonuclease activity, are very useful for DNA sequencing.

SUMMARY OF THE INVENTION

The DNA polymerase of E. coli bacteriophage T5 is distinguished from other DNA polymerases by its high degree of processivity. In other words, a particular T5-DNAP molecule will replicate a single template DNA molecule without dissociation. Das & Fujimura (1977) and (1979), supra, report that T5-DNAP processively synthesizes about 140 to about 200 nucleotides before dissociation. In contrast, other DNA polymerases, such as T4 DNA polymerase, Klenow, and reverse transcriptase, tend to dissociate from the template/newly synthesized strand duplex after only a few bases: a newly synthesized strand will usually have been synthesized by several different enzyme molecules. Similarly, the 3'-to-5' exonuclease activity of T5-DNAP is highly processive; a particular DNA strand will usually be hydrolysed by only one exonuclease molecule. T5-DNAP is also exceptionally good at displacing nicked duplex DNA strands while synthesizing a new strand. Most DNA polymerases need other protein factors or enzymatic activities to accomplish the same result.

These strand displacement and processivity qualities make T5-DNAP a good polymerase to use for DNA sequencing or in a DNA amplification scheme. T5-DNAP does not need a protein co-factor to be active or processive, in contrast to other polymerases useful for the same biochemical tasks. For example, T7 DNA polymerase, which is also processive and often used for DNA sequencing, needs E. coli thioredoxin as a cofactor. Lastly, in infections of E. coli by T5 phage, T5-DNAP is present at very low levels, which increases production costs in using the T5-DNAP. To date, this has made commercial production impractical because acceptable, though less effective, alternatives are available at more reasonable costs. Therefore, it is an object of the present invention to provide improved means for producing T5 DNA polymerase. The 3'-to-5' exonuclease activity of many DNA polymerases is disadvantageous in situations where one is trying to achieve net synthesis of DNA. Therefore it is another object of the present invention to provide a T5-DNAP derivative lacking this exonuclease activity.

The 3'-to-5' exonuclease activity is undesirable for a DNA sequencing enzyme. Therefore, it is an object of the present invention to obtain T5-DNAP lacking 3'-to-5' exonuclease activity. Mutant T5-DNAP lacking 3'-to-5' exonuclease activity is useful to synthesize DNA, and therefore to sequence DNA, using nucleotide analogs which otherwise would not be incorporated because 3'-to-5' editing/exonuclease activity.

The present invention is predicated on several discoveries. Fujimura et al. showed that the gene for T5-DNAP is on the SmaI fragment D. Using this information, it should have been possible to clone the gene using a simple, straightforward cloning strategy. However, Applicant surprisingly discovered that the presence of sequences near the T5-DNAP gene were deleterious to the host cell and thus the gene could not be directly cloned. In order to clone the T5-DNAP gene, the deleterious T5 sequences flanking the T5-DNAP gene, particularly the sequences 5'-to the structural gene, must be removed before it can be cloned in an E. coli host cell.

Leavitt & Ito, Proc. Natl. Acad. Sci. USA 86:4465–4469 (1989) disclosed the cloning of fragments of the T5-DNAP gene and the sequencing thereof. These fragments were not reassembled, nor was expression of the gene obtained. Further, the published sequence of Leavitt & Ito is incorrect at its 5'-end (see FIG. 1). Specifically, an extra "A" residue is reported in the region of nucleotides +45 to +50. This mistake corrupts the open reading frame analysis, leading to an improperly derived sequence for the amino-terminus of the protein, substituting an improper polypeptide of 15 amino acid residues for the correct 11 residue sequence. Use of this sequence to engineer the T5-DNAP gene would leave excess flanking sequences at the 5'-end, which can lower expression levels. Specifically, it has been discovered that with a construction that places a heterologous ribosome binding site immediately next to the translational initiation codon, higher levels of enzyme will be produced than with constructions that are identical except for the retention of small amounts of 5'-flanking sequences. Furthermore, use of the published sequence from Leavitt & Ito, in some types of constructions, can lead to translational initiation out of the correct reading frame. For example, a fusion protein initiating 5'-to the sequencing error disclosed in FIG. 1 would be unexpectedly inoperative. Given the herein disclosed teachings, detailed in the Examples, one of ordinary skill in the art can use standard recombinant DNA techniques to practice the preferred embodiments, namely expression of T5 DNA polymerase in *E. coli*.

BRIEF DESCRIPTION OF THE DRAWINGS

FIG. 1 is a comparison of the sequences disclosed herein with those published by Leavitt & Ito, *Proc. Natl. Acad. Sci. USA* 86:4465–4469 (1989). The upper half of the Figure gives Leavitt & Ito's DNA sequence and the protein sequence derived therefrom. The lower half of the Figure gives a corrected DNA sequence and a corrected protein sequence derived therefrom. The numbering convention is as in Leavitt & Ito. The "AUG" translational start codons are in bold letters, as is the location of extra "A" introduced into the sequence. Note that the exact location of the mistake could be anywhere in the string of "A"s.

DETAILED DESCRIPTION OF THE INVENTION

Figures 2A, 2B, 2C, 2D:
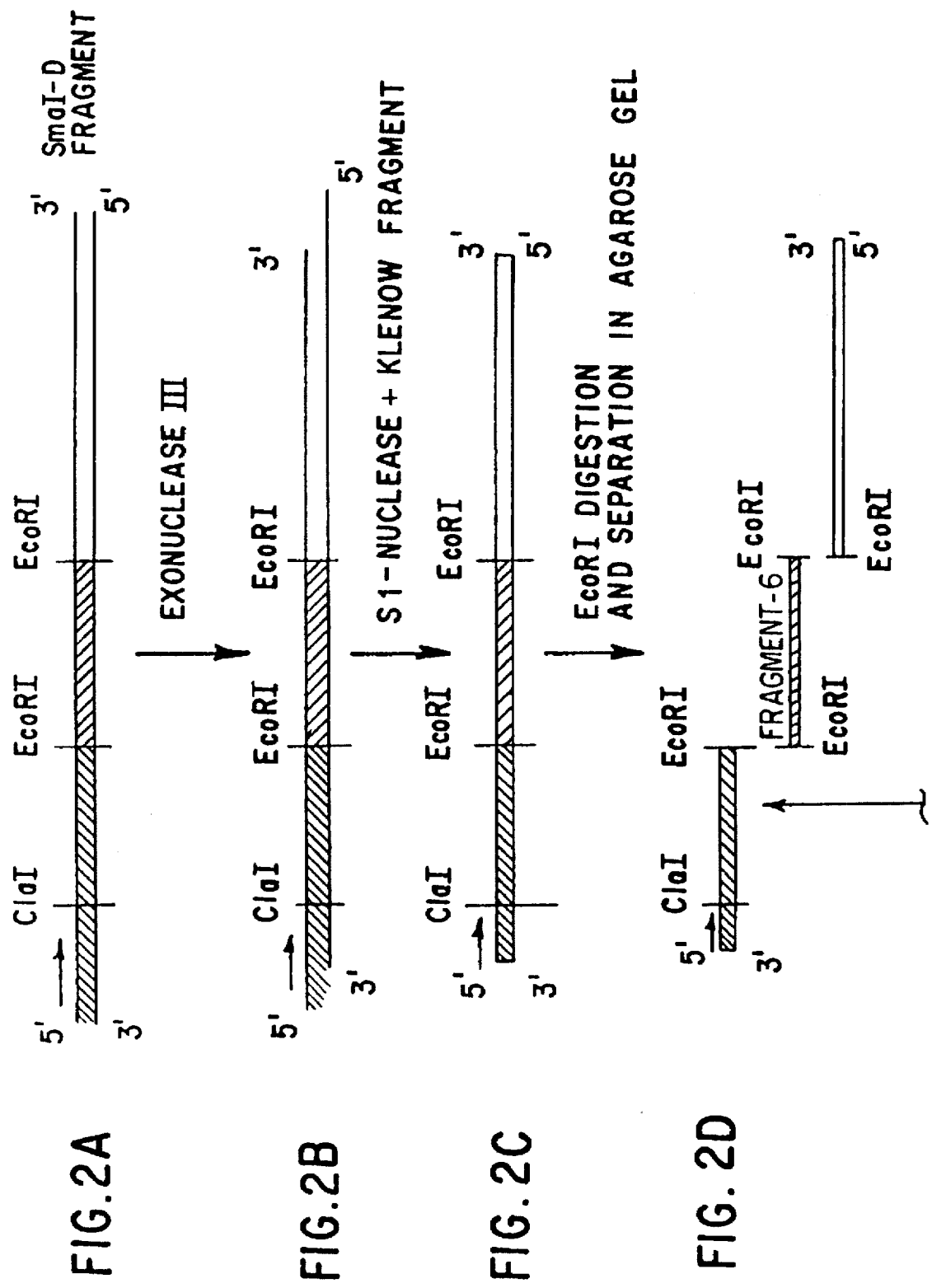
FIGS. 2A-2E are schematic drawings, not necessarily to scale, of many of cloning schemes described in the Examples, and are especially useful in understanding Examples 2 and 6.

The following terms are defined in order to provide a clear and consistent understanding of their use in the specification and the claims. Other terms are well known to the art so that they need not be defined herein.

Amino acid residues are numbered herein as numbered by Leavitt & Ito, supra. Note that the first 15 amino acids disclosed therein are incorrect; the correct N-terminal 11 residues are disclose herein in FIG. 1. Their sequence is correct starting with the $Lys^{16}$ residue, which, if one were to renumber the sequence correctly, would be labeled $Lys^{12}$.

"Structural gene" is a DNA sequence that is transcribed into messenger RNA that is then translated into a sequence of amino acid residues characteristic of a specific polypeptide. As used herein, a structural gene may contain a heterologous ribosome binding site, replacing its natural (homologous) ribosome binding site.

"Nucleotide" is a monomeric unit of DNA or RNA consisting of a sugar moiety, a phosphate, and a nitrogenous heterocyclic base. The base is linked to the sugar moiety via the glycosidic carbon (1' carbon of the penrose). The combination of a base and a sugar is called a nucleoside. Each nucleotide is characterized by its base. The four DNA bases are adenine (A), guanine (G), cytosine (C), and thymine (T). The four RNA bases are A, G, C and uracil (U).

"Processive" is a term of art referring to an enzyme's property of acting to synthesis or hydrolyse a polymer without dissociating from the particular polymer molecule. A processive DNA polymerase molecule can add hundreds of nucleotides to a specific nucleic acid molecule before it may dissociate and start to extend another DNA molecule. Conversely, a non-processive polymerase will add as little as a single nucleotide to a primer before dissociating from it and binding to another molecule to be extended. For the purposes of the present invention, processive refers to enzymes that add, on the average, at least 100, and preferably, about 200 or more, nucleotides before dissociation.

"Thioredoxin" is a enzyme well known to the art that is involved in oxidation and reduction reactions. It is also required as a subunit for T7 DNA polymerase activity. "Thioredoxin-independent" refers to the ability of an enzymatic activity to be active in the absence of thioredoxin.

"Promoter" is a term of art referring to sequences necessary for transcription. It does not include ribosome binding sites and other sequences primarily involved in translation.

"Gene" is a DNA sequence that contains information necessary to express a polypeptide or protein.

"Neterologous" refers herein to two DNA segments having different origins,; i.e. not, in nature, being genetically or physically linked to each other. Neterologous also describes molecules that are in nature physically or genetically linked together but which are linked together in a substantially different way than is found in nature.

"Homology", as used herein, refers to the comparison of two different nucleic acid sequences. For the present purposes, assessment of homology is as a percentage of identical bases, not including gaps introduced into the sequence to achieve good alignment. Per cent homology may be estimated by nucleic acid hybridization techniques, as is well understood in the art as well as by determining and comparing the exact base order of the two sequences.

"Mutation" is any change that alters the DNA sequence. As used herein, a mutated sequence may have single or multiple changes that alter the nucleotide sequence of the DNA. Alterations of the DNA sequence include deletions (loss of one or more nucleotides in the DNA sequence) and/or substitutions (substituting a different nucleotide for the original nucleotide along the DNA sequence).

"Purifying" refers herein to increasing the specific activity of an enzymatic activity over the level produced in a culture in terms of units of activity per weight of protein. This term does not imply that a protein is purified to homogeneity. Purification schemes for T5-DNAP are known to the art.

"Expression" is the process by which a promoter/ structural gene produces a polypeptide. It involves transcription of the gene into messenger RNA (mRNA) and the translation of such mRNA into polypeptide(s).

"Substantially pure" means that the desired purified enzyme is essentially free from contaminating cellular components which are associated with the desired enzyme in nature. Contaminating cellular components may include, but are not limited to, phosphatases, exonucleases or endonucleases.

"Origin of replication" refers to a DNA sequence from which DNA replication is begun, thereby allowing the DNA molecules which contain said origin to be maintained in a host, i.e., replicate autonomously in a host cell.

"3'-to-5' exonuclease activity" is an enzymatic activity well known to the art. This activity is often associated with DNA polymerases, and is thought to be involved in a DNA replication "editing" or correction mechanism.

"Host" is any prokaryotic or eukaryotic microorganism that is the recipient of a DNA molecule. The DNA molecule may contain, but is not limited to, a structural gene, a promoter and/or an origin of replication.

A "DNA polymerase substantially reduced in 3'-to-5' exonuclease activity" is defined herein as either (1) a mutated DNA polymerase that has about or less than 10%, or preferably about or less than 1%, of the specific activity of the corresponding unmutated, wild-type enzyme, or (2) a DNA polymerase having a 3'-to-5' exonuclease specific activity is less than about 1 unit/mg protein, or preferably about or less than 0.1 units/mg protein. A unit of activity of 3'-to-5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Bradford, *Anal. Biochem.* 72:248 (1976). As a means of comparison, natural, wild-type T5-DNAP or T5-DNAP encoded by pTTQ19-T5-2 has a specific activity of about 10 units/mg protein while the DNA polymerase encoded by pTTQ19-T5-2(Exo$^-$) has a specific activity of about 0.0001 units/mg protein, or 0.001% of the specific activity of the unmodified enzyme, a $10^5$-fold reduction.

The present invention discloses a recombinant DNA molecule having: a structural gene encoding a protein which has a processive, thioredoxin-independent DNA polymerase activity; a promoter heterologous to the structural gene; and an origin of replication heterologous to the structural gene. In this combination, the promoter and the structural gene are in such position and orientation with respect to each other that the structural gene may be expressed in a host cell under control of the promoter, and the origin of replication is capable of maintaining the promoter/structural gene/origin of replication combination in a host cell. Preferably, the promoter and the origin of replication are functional in the same host cell, exemplified herein by an *E. coli* host cell. The DNA molecule is preferably contained by a host cell, exemplified herein by an *E. coli* host cell (in particular, *E. coli* BH215 (pTTQ19-T5-2), NRRL B-18526), but may, of course, exist in vitro. The promoter may be inducible, e.g. a lambda $P_L$ promoter or a tac promoter. The protein may also have a processive 3'-to-5' DNA exonuclease activity or may have substantially reduced 3'-to-5' exonuclease activity. Preferably, the structural gene is not under control of a homologous promoter. In the preferred example, the structural gene is under the control of a heterologous ribosome binding site, not a homologous ribosome-binding site.

The structural gene should have at least about 75% homology with T5 DNA polymerase structural gene, and preferably at least about 90% homology, provided that the protein when expressed has T5 DNA polymerase activity. The structural gene may be derived from the T5 DNA polymerase structural gene, and is exemplified herein by the T5 DNA polymerase structural gene. The DNA comprising the T5 DNA polymerase structural gene may be derived from genomic DNA, cDNA, synthetic DNA and combinations thereof.

Alternatively, the structural gene encodes a protein having at least about 75% homology with T5 DNA polymerase, preferably at least about 90% homology, again provided that the protein when expressed has T5 DNA polymerase activity. The structural gene encodes a protein derived from T5 DNA polymerase, and is exemplified herein by a structural gene encoding T5 DNA polymerase. Specific molecules exemplified herein include "clone #2", pTTQ19-T5-2, which is preferred, and functional derivatives thereof. A functional derivative of a DNA molecule is derived from the original DNA molecule but still may express the desired structural gene in a host or in vitro, i.e., express a gene encoding for T5 DNA polymerase activity.

The present invention pertains both to the T5 DNA polymerase and to its functional derivatives. A "functional derivative" of T5 DNA polymerase is a compound which possesses a biological activity (either functional or structural) that is substantially similar to a biological activity of T5 DNA polymerase. The term "functional derivative" is intended to include the "fragments," "variants," "analogues," or "chemical derivatives" of a molecule. A "fragment" of a molecule such as T5-DNAP, is meant to refer to any polypeptide subset of the molecule. A "variant" of a molecule such as T5-DNAP is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analog" of a molecule such as T5-DNAP is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc.

The present invention also discloses a method for production of a protein having a processive, thioredoxin-independent DNA polymerase activity having the steps of culturing a cell containing a recombinant DNA molecule under conditions where the structural gene is expressed, followed by purifying the protein expressed during the culturing step. In this method, the recombinant DNA molecule has a structural gene encoding the protein, as well as a promoter and an origin of replication heterologous to the structural gene. The promoter and the structural gene are in such position and orientation with respect to each other that the promoter may be expressed in a cell under control of the promoter. Also, the origin of replication is heterologous to the structural gene and capable of maintaining the structural gene/promoter/origin of replication combination in the host cell. Expression and maintenance are preferably in an *E. coli* host cell. The promoter may be heterologous to the structural gene and may be inducible, e.g. a lambda $P_L$ promoter or a tac promoter. Preferably, the structural gene is not under control of a homologous promoter. In the preferred embodiment, it is not under control of a homologous ribosome-binding site, being under control of a heterologous ribosome binding site. The protein may have a processive 3'-to-5' DNA exonuclease activity or may have substantially reduced 3'-to-5' exonuclease activity. The structural gene should have at least about 75% homology with a T5 DNA polymerase structural gene, and preferably at least about 90% homology. The structural gene should be derived from a T5 DNA polymerase structural gene, and is exemplified herein by a T5 DNA polymerase structural gene. Alternatively, the structural gene encodes a protein having at least about 75% homology with T5 DNA polymerase, preferably at least about 90% homology, provided that the protein when expressed has T5-DNAP activity. The structural gene encodes a protein derived from T5 DNA polymerase, and is exemplified herein by a structural gene encoding T5 DNA polymerase. Specific DNA molecules exemplified herein include "clone #2", pTTQ19-T5-2, which is preferred, and functional derivatives thereof.

Other promoters, vectors, and host cells, both prokaryotic and eukaryotic, are well known in the art and in keeping with the specification, may be used to practice the invention.

The present invention further discloses a protein having a processive, thioredoxin-independent DNA polymerase activity produced by the method of present invention. This protein may have a processive 3'-to-5' DNA exonuclease activity or may have substantially reduced 3'-to-5' exonuclease activity. The protein should have at least about 75% homology with T5 DNA polymerase, and preferably at least about 90% homology, provided that the T5-DNAP has biological activity. The protein may be derived from, and is herein exemplified by, T5 DNA polymerase.

The T5 DNA polymerase of this invention may be used in cloning and in vitro gene expression experiments to produce heterologous polypeptides from the cloned genes. The T5-DNAP of this invention may also be used for DNA sequencing.

Having now generally described this invention, the same will be better understood by reference to specific examples, which are included herein for purposes of illustration only, and are not intended to be limiting unless otherwise specified.

EXAMPLES

Though the written description that follows is complete and accurate, some may find that overall cloning strategy may be more easily understood by reference to FIGS. 2–6.
Example 1
Isolation of T5 phage DNA Growth of *E. coli* and infection with bacteriophage T5 were done as previously described by Schneider S E et al., *J. Virol.* 56:245–249 (1985).

Purification of T5 phage DNA was isolated by the following procedure. Briefly, *E. coli* F (provided by Dr. Robert K. Fujimura, Oak Ridge National Laboratory, Oak Ridge, Tenn.) was grown in Luria broth at 37° C. to an O.D.550 of about 0.50. $CaCl_2$ was added to a final concentration of 2 mM. T5 phage (nick-less) (provided by Dr. Fujimura) was added at an approximate cell:phage ratio of 15:0.16. The phage-infected cells were shaken very slowly at 37° C. until the O.D.550 decreased from about 0.50 to about 0.2. The cells and the cell debris were removed by centrifugation. The supernatant was saved.

To about 900 ml of this supernatant, DNase I and RNase A were added to final concentrations of 10 µg/ml each and $MgCl_2$ was added at a final concentration of 5 mM. The supernatant was then incubated 30 minutes at room temperature. Solid NaCl was added to 1M and dissolved. Then PEG 6000–8000 (PEG=polyethylene glycol) was added to 10% and dissolved. The mixture was incubated overnight at 4° C. The resultant solution of phage was spun for 15 minutes at 6000 rpm; suspended in 50 ml buffer D (buffer D=50 mM Tris HCl, pH 7.2, 8.5 mM NaCl, 1 mM $MgCl_2$ and 0.1 mM $CaCl_2$).

A portion (25 ml) was mixed slowly with 20 ml chloroform and then spun for 10 minutes. The aqueous, DNA-containing layer (20 ml) was recovered and diluted to 40 ml with 20 ml of buffer D. SDS (sodium dodecyl sulfate) was added to this layer to a concentration of 1%. After mixing slowly, this was incubated at 37° C. for 10 minutes. Water-saturated phenol (25 ml) was added, mixed slowly but thoroughly and then spun to separate the layers. The upper, viscous, DNA-containing layer was removed carefully and extracted once again with phenol. Then an equal volume of water-saturated phenol:$CHCl_3$:isoamyl alcohol (50:48:2 v:v:v) was added, mixed slowly and spun to separate the layer. The DNA-containing viscous layer was removed and an equal volume of buffer D was added.

Figure 2E:
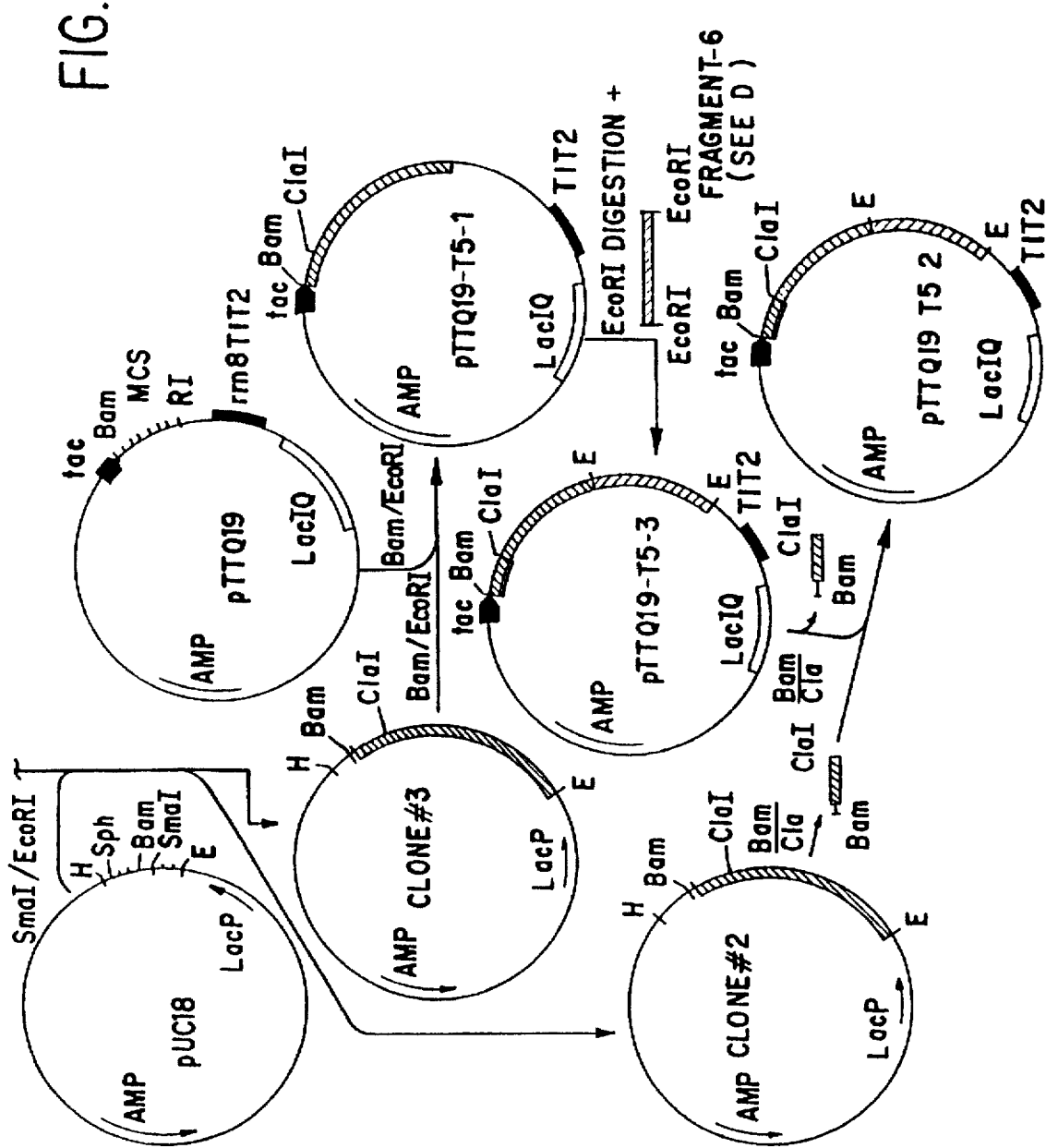

CsCl was added to 1.15 g/ml for purification of the phage DNA by CsCl gradient centrifugation at 40,000 r.p.m. for 2 days. About 9.6 mg of T5 DNA was recovered in 15 ml volume.
Example 2
Exonuclease III and S1 nuclease digestion Initial attempts to clone an intact fragment containing the polymerase gene met with failure. In addition, smaller fragments containing a portion of polymerase gene (5'-end) and the upstream region also could not be cloned. This suggested that the upstream region of the T5-DNAP gene contained either a very strong (e.g. constitutive) promoter or some other sequence(s) lethal to *E. coli*. Therefore, upstream sequences were deleted as follows. A fragment containing entire T5-DNAP gene was generated by SmaI digestion and isolated (FIG. 2, DNA A.). Terminal sequences were then removed from that fragment by treating with exonuclease III (FIG. 2, DNA B.), which removes a single strand of a DNA duplex, attacking from the 3'-ends, and S1 nuclease, which removed single-stranded ends left after exonuclease III treatment. The ends were "polished" with the Klenow fragment of DNA polymerase I in the presence of all four deoxyribonucleotide triphosphates (FIG. 2, DNA C.). The resulting blunt-ended fragment was then digested with EcoRI to facilitate later cloning (FIG. 2, DNAs D.). The following details the above described steps.

SmaI digestion produces four large fragments, the smallest (about 12 kilobase pairs (kbp)) of which has been suggested (Fujimura R et al., *J. Virol.* 53:495–500 (1985)) to contain the intact polymerase gene. Therefore, the smallest SmaI fragment was purified from agarose gels with Gene-Clean™ kits (Bio 101, P.O. Box 2284, La Jolla, Calif. 92038-2284 USA).

Exonuclease III (320 units) was added to approximately 2.5 µg DNA in 100 µl of buffer (50 mM Tris HCl, pH 8.0, 10 mM $MgCl_2$ and 1 mM DTT (DTT=dithiothreitol) was kept at 37° C. At various times aliquots were removed. Each aliquot was placed in its own tube containing 200 mM NaCl, 50 mM EDTA (EDTA=ethylenediamine tetraacetic acid). The tubes were then heated at 70° C. for 10 minutes. The DNA contained therein was ethanol precipitated by addition of 0.1 volumes of 3M sodium acetate, pH 6.0, and 2 volumes of ethanol, and incubation in dry ice for 1 to 2 minutes. The DNA precipitate was collected by being spun for 30 minutes at 14,000 r.p.m. in an Eppendorf microfuge.

The exonuclease III digested DNA was dissolved in 50 μl of S1 nuclease buffer consisting of 30 mM sodium acetate, pH 4.6, 50 mM NaCl, 1 mM zinc acetate, and 9 units of S1 nuclease. The reaction was incubated for 30 minutes at room temperature. After extraction with an equal volume of phenol:CHCl$_3$:isoamyl alcohol, the DNA was ethanol precipitated as described above.

The S1 nuclease treated DNA was redissolved in 30 μl of a buffer containing 50 mM potassium phosphate, pH 7.5, 3 mM MgCl$_2$, 2 mM DTT, 0.1 mM each of dATP, dTTP, dGTP, and dCTP, and 1 unit of the Klenow fragment of *E. coli* DNA polymerase I. The reaction was incubated at room temperature for 5 minutes, extracted with phenol:CHCl$_3$:isoamyl alcohol, and ethanol precipitated as above.

EcoRI cleaves the SmaI fragment isolated above in two places, thereby generating three fragments. The terminally deleted SmaI DNA fragment was digested with EcoRI and the resulting DNA fragments were separated by agarose gel electrophoresis and the bands around 2600 base pairs (bp) in size were purified from the agarose gel by Gene-Clean™ method. These bands of about 2.6 kbp (kilobase pairs) contained two fragments. One fragment was the central of the three EcoRI sub-fragments of the terminally digested SmaI fragment, the other fragment was the shorter of the two end fragments. This end fragment had had its SmaI end trimmed by the exonuclease III/S1 nuclease treatment and had a ClaI site proximal to the "SmaI" end and distal to its EcoRI end. This ClaI site was useful for orienting the fragment, being at the 5'-end of the fragment as defined by the orientation of the T5-DNAP gene.

Example 3
Cloning of a fragment including 5'-flanking sequences

S1 nuclease and Klenow fragment treatment of exonuclease III treated DNA had created a blunt-ended fragment. Later, EcoRI treatment had created a fragment of around 2.6 kbp having a blunt-end on one side (the "SmaI" end, 5'-to the T5-DNAP gene) and sticky EcoRI end on the other. This purified fragment was mixed with and ligated to cloned into pUC18 DNA (Yanisch-Perron C et al., *Gene* 33:103–119 (1985)) which had been previously digested with SmaI and EcoRI. (Note that though the 2.6 kbp band contained two different fragments, the 2.6 kbp "end" fragment was preferentially cloned because the internal fragment lacked a blunt end, i.e. its ends did not match those of the vector.) This cloning operation destroyed the SmaI site but preserved the EcoRI site. Six different clones having inserts of varying lengths (but all are around 2.6 kbp) were isolated. One of them, labeled #3, was chosen for further work because this clone contained the largest fragment, i.e the smallest deletion. DNA sequencing showed that the T5 sequences of clone #3 started at nucleotide −98 in the sequence of Leavitt & Ito, supra.

The fragment 3'-to the 2.6 kbp fragment cloned present in clone #3 was placed behind the 2.6 kbp clone #3 fragment. In other words, the 2.6 kbp internal EcoRI fragment was placed ligated to the 2.6 kbp "end" fragment in the orientation which reproduces that found in T5 virus. This was done in an expression vector, pTTQ19 (Stark M J R, *Gene* 51:255–267 (1987); available from Amersham, International, plc).

pTTQ19 DNA was digested with BamHI and EcoRI and then mixed with and ligated to the 2.6 kbp BamHI/EcoRI fragment of clone #3. The BamHI site was present (in the multiple cloning site (polylinker) of pUC18) next to the SmaI site which had been used to clone the 2.6 kbp fragment of clone #3. The resulting clone was reopened with EcoRI and mixed with and ligated to T5 EcoRI fragment 6 in order to introduce any missing 3'-end (carboxyl-terminus encoding end) of T5 polymerase gene. (Note that EcoRI fragment 6 can be isolated clean of other T5 sequences, the mixture of two 2.6 kbp fragments was due to an additional cleavage with SmaI.) The resultant clone, pTTQ19-T5-3, produced significant amounts of polymerase activity only after induction with IPTa. Production of T5-DNAP activity in pTTQ19-T5-3-containing cells was estimated to be equal to that found in phage-infected cells.

Example 4
Optimization of the 5'-end of the T5-DNAP gene

Clone #3 was selected from among other clones made at the same time because it had the smallest deletion of those screened. Sequencing of the 5'-end region of clone #3 and comparison with the published sequence (Leavitt & Ito, supra) showed that the T5 DNA insert of clone #3 carried a promoter-like sequence and a ribosome-binding-site. Apparently, however, the promoter-like sequence is not functional; rather, its presence reduces production of T5 DNAP from the tac' promoter. Therefore, larger deletions were introduced into pTTQ19-T5-3 to see their effect on enzyme production.

The 5'-end of the clone #3 T5 DNA was removed from pTTQ19-T5-3 by digestion with BamHI and ClaI. BamHI/ClaI fragments from independently derived clones, produced in the same experiment that produced clone #3, individually mixed with and ligated to aliquots this DNA. Transformants containing the resultant clones were screened for T5-DNAP production; larger deletions were observed to produce more enzyme. The clone which produced the highest level of T5-DNAP was estimated by gel electrophoretic analysis to lack all of the presumptive promoter region and the presumptive ribosome binding site. DNA sequencing confirmed that, the 5'-end of the T5 DNA polymerases structural gene is at nucleotide +12, as numbered by Leavitt & Ito, supra. This clone, labeled pTTQ19-T5-2, produced about 8 times more enzymatic activity than pTTQ19-T5-3; cells harboring this plasmid made about 12-fold more units of enzyme than virus-infected cells.

*E. coli* BH215 (pTTQ19-T5-2) was deposited under the Budapest Treaty with an International Depository Authority, the Patent Culture Collection, Northern Regional Research Center, USDA, 1815 N. University St., Peoria, Ill. 61604 USA, as NRRL B-18526. It was accessioned on Jul. 27, 1989, and will be made available to the public upon grant of Letters Patent or publication of this application. Availability of this material is not necessary for practice of the present invention, which may be performed using the teachings of the present disclosure in combination with publicly available materials and information and techniques well known in the arts of molecular biology, recombinant DNA, and chimeric gene expression. This strain is best maintained on Luria broth supplemented with 100 mg/l ampicillin and 0.2% glucose, to fully repress the tac promoter (see Stark, supra), at 30° C., which lowers the copy number of pUC-based plasmids, thereby lowering the chances of picking up a mutation.

Example 5
Miscellaneous experiments

Thioredoxin is necessary for production of T5 phage; an *E. coli* mutant deficient for thioredoxin did not support growth of T5 while an isogeneic strain did. In contrast, active T5-DNAP is made in the deficient strain if it harbors a clone that can express T5-DNAP. Furthermore, addition of thioredoxin in reactions containing T5-DNAP made in a thioredoxin-deficient strain did not affect activity. Therefore, thioredoxin is not an accessory protein to the polymerase and has some other function in the T5 life cycle.

The BamHI/ClaI fragment of clone #3 was sub-cloned as a BamHI-blunt fragment by treating ClaI-digested DNA with Klenow fragment and then digesting with BamHI into M13mp18 and M13mp19 at BamHI/SmaI sites, which are identical except for the orientation of their poly-linkers (Yanisch-Perron et al., supra). This fragment, about 650 bp in length, has the pUC18 poly-linker BamHI site at one end and the T5 ClaI site present near the "5'-end" of the 2.6 kbp "end fragment" at the other end. More than 300 times more clones were observed with the M13mp18 vector, where the T5 fragments was in the opposite orientation to be transcribed by the lac promoter of the pUC vector, than with M13mp19, where it is the correct orientation. The BamHI/ClaI fragment represents the amino-terminal end of T5 DNAP protein and the 3'-to-5' exonucleases of several DNA polymerases are known to be present in the amino-terminal region. Therefore, it is likely that this region of the T5-DNAP gene encodes the 3'-to-5' exonuclease activity, thus suggesting that expression of this activity in the absence of the polymerase activity may be detrimental to *E. coli.*

Example 6
Cloning of 5'-end of structural gene of T5-DNAP

Figure 3:
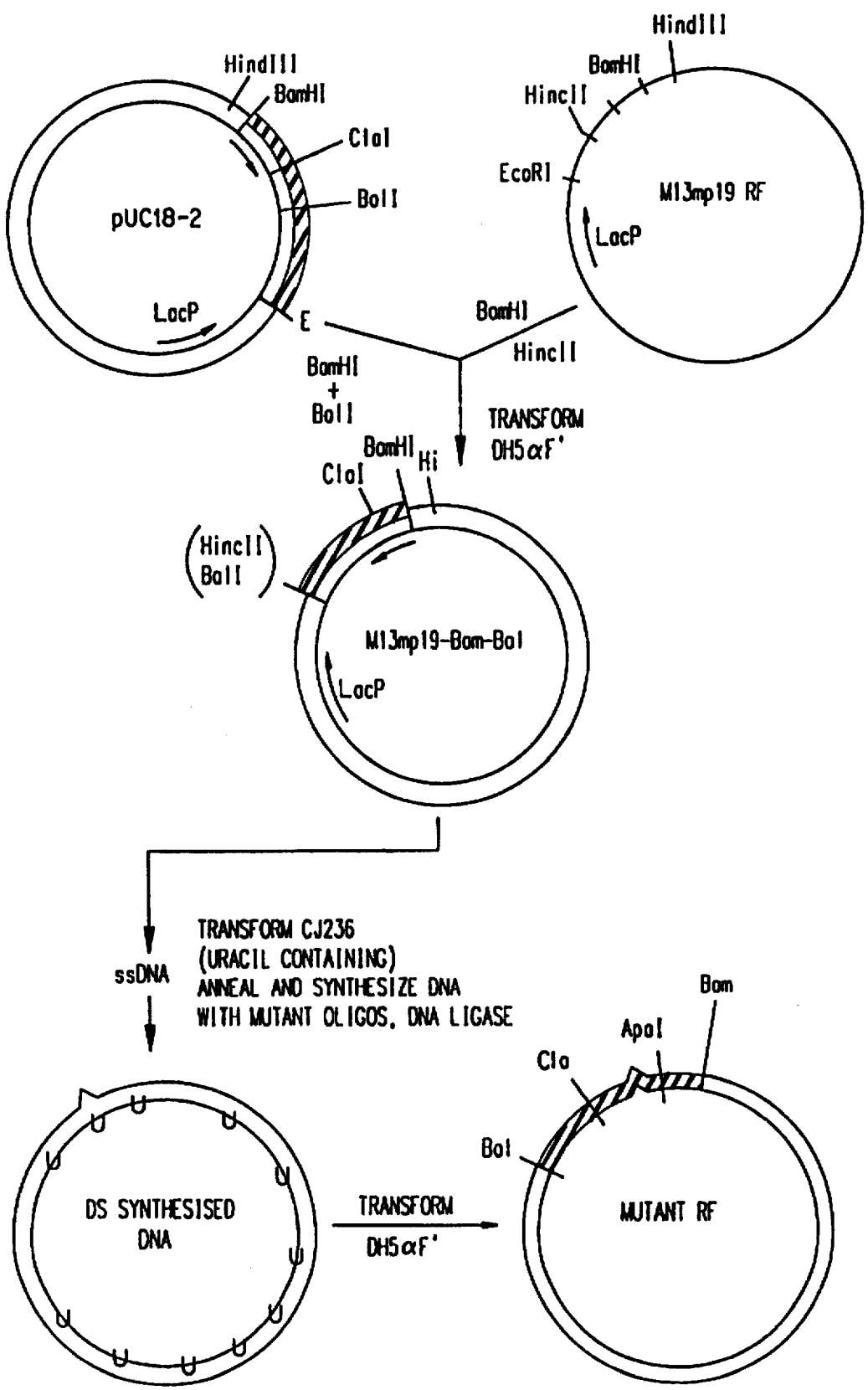
FIG. 3 is a schematic drawing, not necessarily to scale, of the preparation of a "mutant RF" (Example 6, see also Example 8).

A BamHI/BalI fragment about 850 bp in length, was sub-cloned into M13mp19 as follows. About 1 µg of clone #2 (FIG. 2) DNA was digested with BamHI and BalI. The approximately 850 bp fragment was purified from a agarose gel after electrophoresis by a Gene Clean™ Kit (Bio101, P.O. Box 2284, La Jolla, Calif. 92038). About 1 µg of M13mp19 DNA was digested with BamHI and HincII and ligated with 850 bp BamHI/BalI fragment. The result of this operation was that the fragment was cloned in an translational polarity opposite to the polarity of lac promoter present in the M13mp19 vector (FIG. 3). Therefore, expression of cloned gene product was eliminated. Cloning of a BamHI/ClaI fragment of T5-DNAP gene in the same polarity as the lac promoter was found to be deleterious for the cell (see example 5). This implied that the exonuclease domain may be present in the amino-terminal end of the protein or 5'-end of the gene. The ligated DNA was introduced into *E. coli* DH5αF' cells by a standard method. Clones containing the fragments were selected and phage stocks of the desired clones were saved as described by BioRad's Muta-Gene™ M13 in vitro mutagenesis kit (BioRad Laboratories, 1414 Harbour Way South, Richmond, Calif. 94804). Uracil-containing single-stranded DNA (ssDNA) was isolated from dut⁻ ung⁻ CJ236 host cells by the method described in the kit.

Example 7
Design of a primer for in vitro mutagenesis

As explained in Examples 5 and 6, 3'-to-5' exonuclease domain of T5-DNAP probably was at the 5'-end of the structural gene. Site of mutagenesis within this region was chosen by analogy with the *E. coli* DNA polymerase I. T5-DNAP was suggested to be highly related to *E. coli* DNA polymerase I, (Leavitt M C & Ito J, *Proc. Natl. Acad. Sci. USA* 86:4465–4469 (1989)).

The amino acids Asp[355] and Glu[357] of *E. coli* DNA polymerase I and Asp[138] and Glu[140] of T5-DNAP in the sequence of Leavitt & Ito, supra, are conserved. The amino acids Asp[355] and Glu[357] of *E. coli* DNA polymerase I were suggested to be involved in 3'-to-5' exonuclease activity by Joyce C M & Steitz T A (*Trends Biochem. Sci.* 12:288–292 (1987)). Similar conserved amino acids between *E. coli* DNA polymerase I and T7 DNA polymerase were also found (Leavitt and Ito, supra; Johnson et al., 8th Summer Symposium in Molecular Biology, "DNA protein interaction" Penn St Univ., Jul. 26–28, 1989). Johnson et al. showed that changing of Asp[5] and Glu[7] of T7 DNA polymerase to Ala[5] and Ala[7] resulted in the reduction of 3'-to-5' exonuclease activity 10⁴-fold relative to native T7 DNA polymerase. Tabor S & Richardson C C (*J. Biol. Chem.* 264:6447–4658 (1989)), on the other hand, showed that deletion of Ser[122] and His[123] of T7 DNA polymerase reduced the 3'-to-5' exonuclease activity to less than 0.001% of the activity of native T7 DNA polymerase. Results of Johnson et al. and of Tabor and Richardson suggest that exonuclease domain is in the 5'-end of the gene, however, mutation in two different locations resulted in loss of 3'-to-5' exonuclease activity. Therefore, a mutation was made in the T5-DNAP based upon the analogy with both *E. coli* DNA polymerase I and T7 DNA polymerase (i.e. changing Asp[138] and Glu[140] in the T5-DNAP protein, as numbered by Leavitt and Ito, supra). Therefore, an oligonucleotide with the following sequence was made by using standard techniques:

5' G GTT ATC GGG CCC GTC GCA TTC GCC TCC GCA ACC TCA GCA C 3'

(Underlined bases indicate substitutions relative to the native sequences and spaces delineate the polypeptide-encoding codons.) This oligonucleotide changes the native Asp[138] and the native Glu[140] to Ala[138] and Ala[140], respectively. The sequence 5'GGGCCC3' was introduced into this oligonucleotide without changing the encoded amino acid. This aided identification of mutant DNA by formation of an easily screenable ApaI site.

The oligonucleotide designed above was synthesized by standard methods and were phosphorylated by T4 polynucleotide kinase.

Example 8
In vitro mutagenesis of T5-DNAP

The uracil-containing ssDNA isolated in Example 6 was annealed with the oligonucleotide designed and prepared in Example 7. The oligonucleotide/ssDNA complex was polymerized using T4 DNA polymerase and T4 DNA ligase in the presence of all four deoxyribonucleotides using BioRad Muta-Gene™ kit. The synthesized DNA was introduced into *E. coli* DH5αF' cells. The clones with mutant oligonucleotides were screened for the presence of ApaI site. Clones that contained an ApaI site were presumed to be mutant clones. Mutant clones derived from each oligonucleotide were pooled to form a "mutant RF" (FIG. 3).

Example 9
Introduction of mutant fragment into pTTQ19-T5-2

Figure 4:
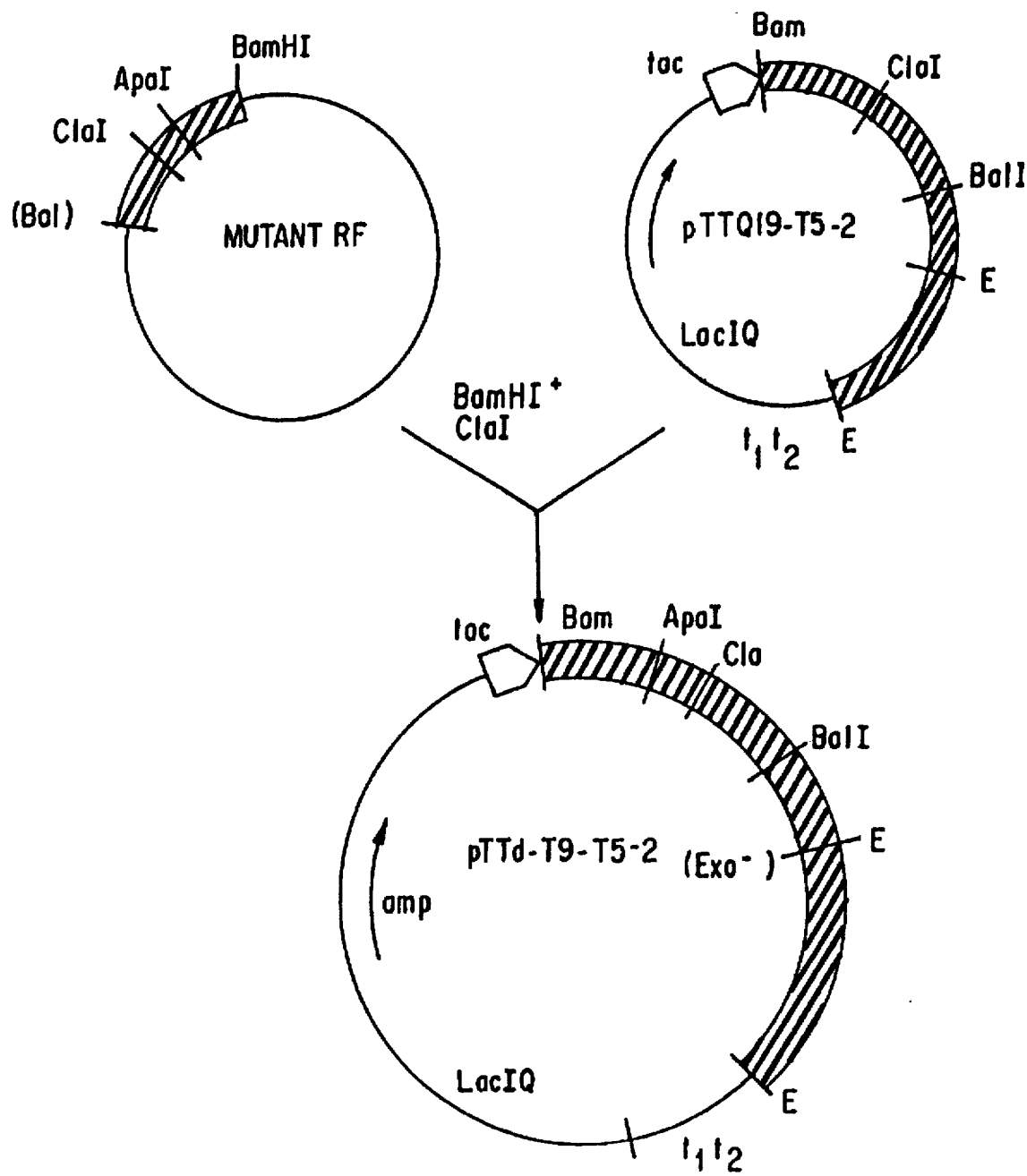
FIG. 4 is a schematic drawing, not necessarily to scale, of pTTQ19-T5-2(Exo⁻) (Example 9).

BamHI/ClaI digestion of mutant RF (FIG. 4) generates 4 fragments. The smallest (about 500 bp) of these fragments contains the mutated sequence having an ApaI site. This fragment was purified from an agarose gel as describes in Example 2. pTTQ19-T5-2 DNA was digested with BamHI and ClaI and the smallest fragment was replaced by the BamHI-ClaI fragments of the mutant RF8 (FIG. 4). The correct assembly of the resulting DNA construction was verified by checking for the presence of an ApaI site between the BamHI and ClaI sites. Several cell lines containing plasmids with the mutant fragment were assayed for polymerase and 3'-to-5' exonuclease activities. A plasmid having a properly inserted mutation and expressing T5 DNA polymerase activity was designated pTTQ19-T5-2(Exo⁻).

Example 10
Placement of T5-DNAP genes behind lambda promoters

Placement the T5-DNAP gene under control of a bacteriophage lambda $P_L$ promoter took advantage of NdeI sites covering the ATG translational start sites of the T5-DNAP and T5-DNAP-Exo⁻ genes and an NdeI site after the lambda $P_L$ promoter of pKD1 (Kotewicz M et al., *Gene* 35:249–259 (1985)).

Figure 5:
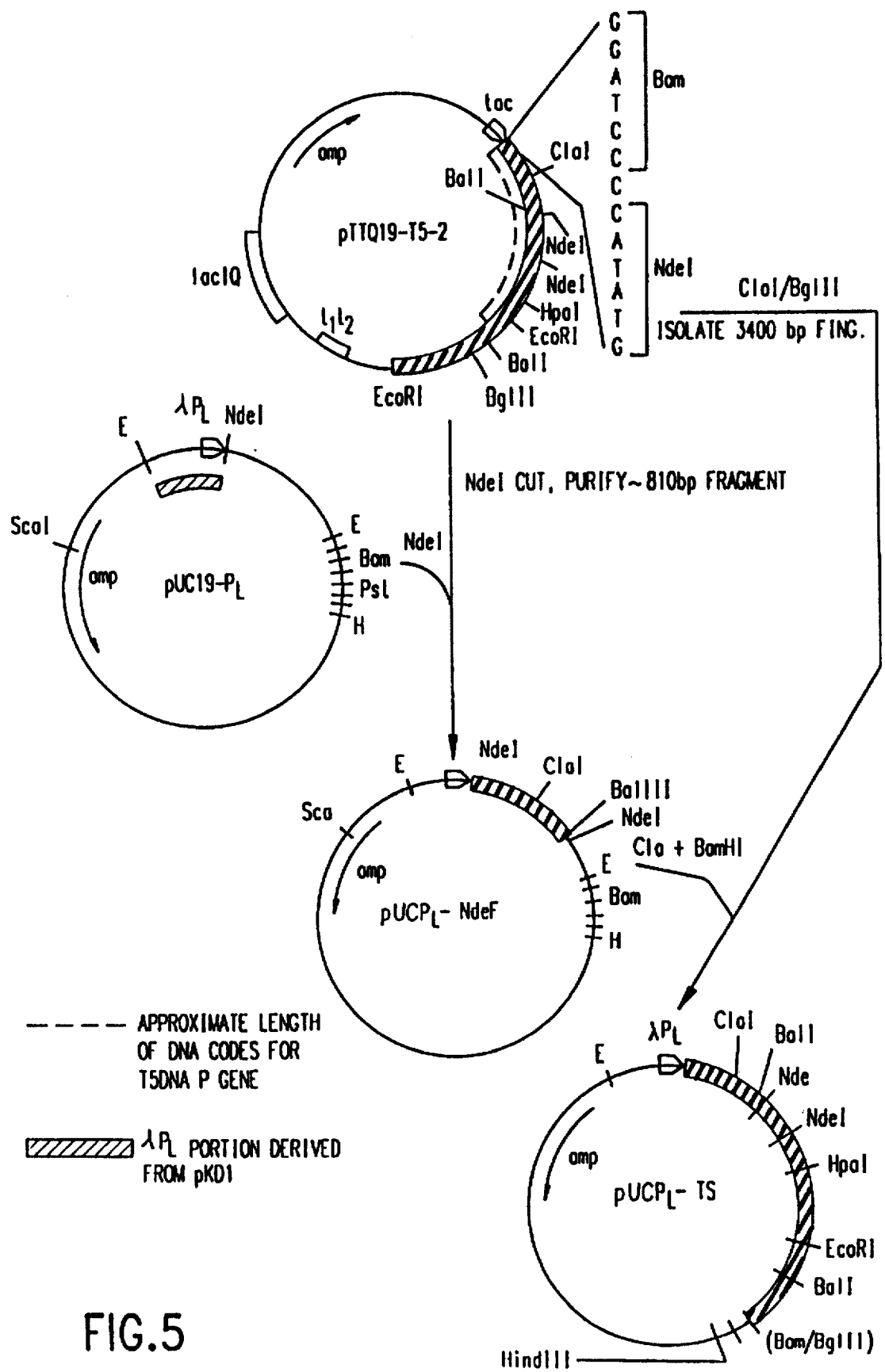
FIG. 5 is a schematic drawing, not necessarily to scale, of a construction having the T5-DNAP gene under control of the lambda $P_L$ promoter (Example 10).
Figure 6:
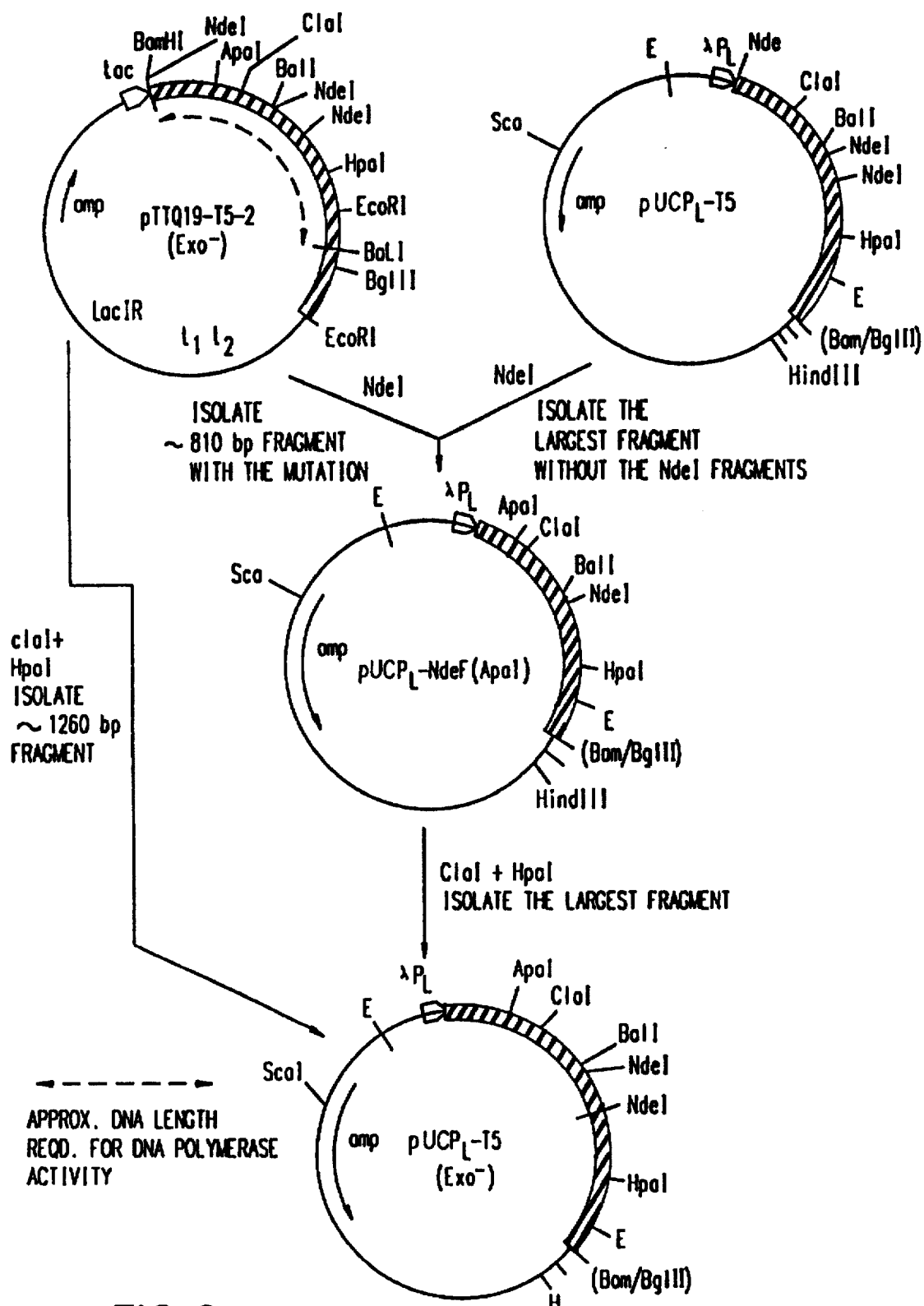
FIG. 6 is a schematic diagram, not necessarily to scale, of construction of an exonuclease deficient mutant of T5 DNAP under control of the lambda $P_L$ promoter (Example 10).

A 0.81 kbp fragment was isolated from NdeI-cut pTTQ19-T5-2. This fragment, which carried a 5'-portion of the T5-DNAP structural gene, was mixed with and ligated to NdeI-linearized pUC19-$P_L$. Proper orientation of the resultant plasmid, pUCP$_L$-NdeF, was verified by relative positions of the BalI site of the insert and the BamHI site of the vector. pUCP$_L$-NdeF DNA was cut with BamHI and ClaI and then mixed with and ligated to a purified, 3.4 kbp ClaI/BgeII fragment of pTTQ19-T5-2, which carried a 3'-portion of the T5-DNAP structural gene. The resultant plasmid, pUCP$_L$-T5, had a complete T5-DNAP structural gene expressible under control of a lambda $P_L$ promoter (FIG. 5).

pUCP$_L$-T5 DNA was digested with NdeI and the largest fragment, which lacked a 3'-portion of the T5-DNAP structural gene, was isolated. pTTQ19-T5-2(Exo⁻) was digested with NdeI and a 0.81 kbp fragment, carrying a 5'-portion of the mutated T5-DNAP gene, was isolated. These two fragment were mixed with each other and ligated together to form pUCP$_L$-NdeI(ApaI), which lacked a central portion of the T5-DNAP structural gene. This plasmid was cut with ClaI and HpaI and the largest resulting fragment, deleted for a central portion of the T5-DNAP gene, was isolated. This fragment was mixed with and ligated to a 1.26 kbp ClaI/HpaI fragment of pTTQ19-T5-2(Exo⁻). The resulting plasmid, pUCP$_L$-T5(Exo⁻), carried a complete T5-DNAP-Exo⁻ structural gene under control of a lambda $P_L$ promoter (FIG. 6).

Example 11

3'-to-5' exonuclease activity in the mutant protein

T5 DNA polymerase purified from *E. coli* cells containing either pTTQ19-T5-2-Exo⁻ or pUCP$_L$-T5(Exo⁻) exhibited about $10^5$-fold less 3'-to-5' exonuclease activity compared to native T5 DNA polymerase isolated from phage infected cells or from cells harboring the plasmid pTTQ19-T5-2. 3'-to-5' exonuclease activity was determined by the procedure described above in the Detailed Description of the Invention in the definition of "DNA polymerase substantially reduced in 3'-to-5' exonuclease activity". Unmodified T5 DNAP has a 3'-to-5' exonuclease specific activity of about 10 units/mg protein. In contrast, the mutated DNA polymerase of the present invention had a 3'-to-5' specific activity of $1 \times 10^{-4}$ units/mg protein.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

---

What is claimed is:

1. A DNA molecule coding for a mutant T5 DNA polymerase protein having a processive, thioredoxin-independent DNA polymerase activity and substantially reduced 3'-to-5' exonuclease activity.

2. The DNA molecule of claim 1, wherein said molecule codes for a mutant T5 DNA polymerase having the amino acid $Asp^{138}$ deleted or substituted with a different amino acid.

3. The DNA molecule of claim 1, wherein said molecule codes for a mutant T5 DNA polymerase having the amino acid $Ala^{138}$ substituted for $Asp^{138}$ of wild type T5 DNA polymerase.

4. The DNA molecule of claim 1, wherein said molecule codes for a mutant T5 DNA polymerase having the amino acid $Glu^{140}$ deleted or substituted with a different amino acid.

5. The DNA molecule of claim 1, wherein said molecule codes for a mutant T5 DNA polymerase having the amino acid $Ala^{140}$ substituted for $Glu^{140}$ of wild type T5 DNA polymerase.

6. The DNA molecule of claim 1, wherein said mutant T5 DNA polymerase a 3'-to-5' exonuclease activity of about or less than 1 unit/mg protein.

7. The DNA molecule of claim 1, wherein said mutant T5 DNA polymerase has a 3'-to-5' exonuclease activity of about or less than 0.1 unit/mg protein.

8. The DNA molecule of claim 1, wherein said mutant T5 DNA polymerase has a 3'-to-5' exonuclease activity of about or less than 0.003 unit/mg protein.

9. The DNA molecule of claim 1, wherein said mutant T5 DNA polymerase has a 3'-to-5' exonuclease activity of about or less than 0.0001 unit/mg protein.

10. A DNA molecule coding for a mutant T5 DNA polymerase protein having a processive, thioredoxin-independent DNA polymerase activity and less than 10% of the 3'-to-5' exonuclease activity associated with the native T5 DNA polymerase.

11. The DNA molecule of claim 1, further comprising a promotor heterologous to the coding sequence for said protein, wherein the promotor and coding sequence are in a position and orientation with respect to each other such that the coding sequence may be expressed in a host cell under control of the promotor; and wherein said DNA molecule also comprises an origin of replication heterologous to the coding sequence and capable of maintaining the promotor/coding sequence/origin of replication combination in the host cell.

12. The DNA molecule of claim 11, wherein the promotor and the origin of replication are functional in the same host cell.

13. The DNA molecule of claim 12, wherein said host cell is *E. coli*.

14. The DNA molecule of claim 1, wherein said molecule has at least about 75% homology with the wild type DNA polymerase gene.

15. The DNA molecule of claim 1, wherein said molecule has at least about 90% homology with the wild type DNA polymerase gene.

16. The DNA molecule of claim 1, wherein said molecule has at least about 99% homology with the wild type DNA polymerase gene.

17. The DNA molecule of claim 1, which is pTTQ19-T5-2 (Exo$^-$).

18. The DNA molecule of claim 1, wherein said polymerase is capable of synthesizing a polynucleotide having an average of at least 100 nucleotides before dissociation.

19. The DNA molecule of claim 1, wherein said polymerase is capable of synthesizing a polynucleotide having an average of at least 200 nucleotides before dissociation.

20. A host cell transformed with the DNA molecule of claim 1.

21. A host cell transformed with the DNA molecule of claim 11.

* * * * *

UNITED STATES PATENT AND TRADEMARK OFFICE
CERTIFICATE OF CORRECTION

PATENT NO. : 5,716,819

DATED : February 10, 1998

INVENTOR : Deb K. Chatterjee

It is certified that an error appears in the above-identified patent and that said Letters Patent is hereby corrected as shown below.

In column 16, line 57, after "polymerase" insert --has--.

In column 17, lines 8, 11, 13 and 16, change "promotor" to --promoter--.

Signed and Sealed this

Second Day of June, 1998

Attest:

BRUCE LEHMAN

*Attesting Officer*          *Commissioner of Patents and Trademarks*